(12) United States Patent
Puah et al.

(10) Patent No.: US 8,885,040 B2
(45) Date of Patent: Nov. 11, 2014

(54) METHOD AND APPARATUS FOR 3-DIMENSIONAL VISION AND INSPECTION OF BALL AND LIKE PROTRUSIONS OF ELECTRONIC COMPONENTS

(75) Inventors: Yong Joo Puah, Singapore (SG); Hak Wee Tang, Singapore (SG); Soon Poo Teo, Singapore (SG)

(73) Assignee: Generic Power Pte Ltd., Singapore (SG)

( * ) Notice: Subject to any disclaimer, the term of this patent is extended or adjusted under 35 U.S.C. 154(b) by 1447 days.

(21) Appl. No.: 12/305,835

(22) PCT Filed: Mar. 30, 2007

(86) PCT No.: PCT/SG2007/000088
§ 371 (c)(1),
(2), (4) Date: Dec. 19, 2008

(87) PCT Pub. No.: WO2007/149050
PCT Pub. Date: Dec. 27, 2007

(65) Prior Publication Data
US 2010/0328435 A1 Dec. 30, 2010

(30) Foreign Application Priority Data
Jun. 21, 2006 (SG) .............................. 200604252-7

(51) Int. Cl.
*G01N 21/00* (2006.01)
*G01N 21/86* (2006.01)
(Continued)

(52) U.S. Cl.
CPC .......... *G01B 11/0608* (2013.01); *G06T 7/0004* (2013.01); *G06T 7/0018* (2013.01);
(Continued)

(58) Field of Classification Search
CPC G01B 11/0608; G06T 7/0006; G06T 7/0075; G06T 2207/10152; G06T 2207/30152; G06T 2207/10012; G06T 7/0004; G06T 7/0018; G06T 7/004; G06T 2207/30244; G06T 2207/30148; G06T 2200/04; G01N 21/8806; G01N 21/95684; G01N 21/951; H04N 13/0329; H04N 13/0242; H04N 13/0246; H04N 13/0253
USPC ........................ 348/47; 382/147, 150; 702/81
See application file for complete search history.

(56) References Cited

U.S. PATENT DOCUMENTS 4,677,473 A * 6/1987 Okamoto et al. ............. 348/126
5,060,065 A * 10/1991 Wasserman ................... 348/131
(Continued)

FOREIGN PATENT DOCUMENTS

EP 1619623 A1 * 1/2006

OTHER PUBLICATIONS

Newton, Harry. "Newton's Telecom Dictionary" 2006, CMP Books, 22nd ed. p. 468.*

*Primary Examiner* — Daniel C Murray
(74) *Attorney, Agent, or Firm* — Ohlandt, Greeley, Ruggiero & Perle, LLP

(57) ABSTRACT

A method for 3-dimensional vision inspection of objects, such as microelectronic components, which have protrusions as features to be inspected, such as input/output contact balls, is disclosed. The method comprises the steps of determining interior and exterior parameters of a stereo camera system, forming a rectified stereo camera system with a rectified camera coordinate system from the parameters of the stereo cameras determined above. A pair of images of the object having a plurality of co-planar protrusions on one surface is captured by the stereo cameras system and is transformed into the rectified coordinate system to form a pair of rectified images. Conjugate points of each protrusion are then determined in the rectified images for the measurement of its location, co-planarity and height. Various configurations of the apparatus for capturing the images and processing the image data are also disclosed.

18 Claims, 8 Drawing Sheets

(51) Int. Cl.

| | | |
|---|---|---|
| *G01N 37/00* | (2006.01) | |
| *G06K 9/00* | (2006.01) | |
| *H04N 7/18* | (2006.01) | |
| *H04N 13/02* | (2006.01) | |
| *G01B 11/06* | (2006.01) | |
| *G06T 7/00* | (2006.01) | |
| *G01N 21/88* | (2006.01) | |
| *G01N 21/956* | (2006.01) | |
| *H05K 13/08* | (2006.01) | |
| *G01N 21/95* | (2006.01) | |

(52) U.S. Cl.
CPC ....... *G06T 7/004* (2013.01); *G06T 2207/30244* (2013.01); *G06T 2207/30148* (2013.01); *G06T 2200/04* (2013.01); *G01N 21/8806* (2013.01); *G01N 21/951* (2013.01); *G01N 21/95684* (2013.01); *G06T 7/0006* (2013.01); *G06T 7/0075* (2013.01); *G06T 2207/10012* (2013.01); *G06T 2207/10152* (2013.01); *G06T 2207/30152* (2013.01); *H04N 13/0239* (2013.01); *H04N 13/0242* (2013.01); *H04N 13/0246* (2013.01); *H04N 13/0253* (2013.01); *H05K 13/08* (2013.01)
USPC ........ 348/126; 250/559.34; 348/47; 348/131; 356/237.4; 382/150; 702/81

(56) References Cited

U.S. PATENT DOCUMENTS

| | | | | |
|---|---|---|---|---|
| 5,383,013 A * | 1/1995 | Cox | | 356/2 |
| 5,465,152 A * | 11/1995 | Bilodeau et al. | | 356/602 |
| 5,546,189 A * | 8/1996 | Svetkoff et al. | | 356/602 |
| 5,550,763 A * | 8/1996 | Michael et al. | | 702/155 |
| 5,574,668 A * | 11/1996 | Beaty | | 702/150 |
| 5,574,801 A * | 11/1996 | Collet-Beillon | | 382/150 |
| 5,654,800 A * | 8/1997 | Svetkoff et al. | | 356/602 |
| 5,828,449 A * | 10/1998 | King et al. | | 356/237.1 |
| 5,859,924 A * | 1/1999 | Liu et al. | | 382/145 |
| 5,870,489 A * | 2/1999 | Yamazaki et al. | | 382/151 |
| 5,926,557 A * | 7/1999 | King et al. | | 382/149 |
| 5,943,125 A * | 8/1999 | King et al. | | 356/237.1 |
| 6,023,663 A * | 2/2000 | Kim | | 702/81 |
| 6,055,054 A * | 4/2000 | Beaty et al. | | 356/601 |
| 6,064,756 A * | 5/2000 | Beaty et al. | | 382/146 |
| 6,064,757 A * | 5/2000 | Beaty et al. | | 382/147 |
| 6,072,898 A * | 6/2000 | Beaty et al. | | 382/146 |
| 6,134,013 A * | 10/2000 | Sirat et al. | | 356/602 |
| 6,144,453 A * | 11/2000 | Hallerman et al. | | 356/616 |
| 6,177,682 B1 * | 1/2001 | Bartulovic et al. | | 250/559.44 |
| 6,522,777 B1 * | 2/2003 | Paulsen et al. | | 382/154 |
| 6,525,331 B1 * | 2/2003 | Ngoi et al. | | 250/559.34 |
| 6,614,926 B1 * | 9/2003 | Fix et al. | | 382/150 |
| 6,778,282 B1 * | 8/2004 | Smets et al. | | 356/614 |
| 6,826,298 B1 * | 11/2004 | O'Dell et al. | | 382/149 |
| 6,862,365 B1 * | 3/2005 | Beaty et al. | | 382/145 |
| 6,915,006 B2 * | 7/2005 | Beaty et al. | | 382/145 |
| 6,915,007 B2 * | 7/2005 | Beaty et al. | | 382/145 |
| 6,937,753 B1 * | 8/2005 | O'Dell et al. | | 382/141 |
| 6,956,963 B2 * | 10/2005 | Ulrich et al. | | 382/154 |
| 7,034,272 B1 * | 4/2006 | Leonard et al. | | 250/208.1 |
| 7,079,678 B2 * | 7/2006 | Beaty et al. | | 382/145 |
| 7,085,411 B2 * | 8/2006 | Beaty et al. | | 382/154 |
| 7,423,743 B2 * | 9/2008 | Smets et al. | | 356/237.1 |
| 7,508,974 B2 * | 3/2009 | Beaty et al. | | 382/145 |
| 7,570,798 B2 * | 8/2009 | Beaty et al. | | 382/145 |
| 7,653,237 B2 * | 1/2010 | Beaty et al. | | 382/145 |
| 7,729,528 B2 * | 6/2010 | O'Dell et al. | | 382/149 |
| 7,751,611 B2 * | 7/2010 | Akiyama et al. | | 382/147 |
| 7,755,376 B2 * | 7/2010 | Ding | | 324/750.07 |
| 8,286,780 B2 * | 10/2012 | Malek et al. | | 198/403 |
| 8,345,252 B2 * | 1/2013 | Nisper et al. | | 356/445 |
| 8,406,619 B2 * | 3/2013 | Cameron et al. | | 396/325 |
| 8,408,379 B2 * | 4/2013 | Malek et al. | | 198/403 |
| 2002/0034324 A1 * | 3/2002 | Beaty et al. | | 382/145 |
| 2002/0037098 A1 * | 3/2002 | Beaty et al. | | 382/145 |
| 2004/0099710 A1 * | 5/2004 | Sommer | | 228/103 |
| 2004/0150822 A1 * | 8/2004 | Yu et al. | | 356/394 |
| 2004/0175029 A1 * | 9/2004 | Fang et al. | | 382/145 |
| 2005/0008218 A1 * | 1/2005 | O'Dell et al. | | 382/145 |
| 2005/0111726 A1 * | 5/2005 | Hackney et al. | | 382/145 |
| 2005/0190960 A1 * | 9/2005 | Beaty et al. | | 382/150 |
| 2005/0190961 A1 * | 9/2005 | Beaty et al. | | 382/150 |
| 2007/0080703 A1 * | 4/2007 | Ding | | 324/765 |
| 2007/0183645 A1 * | 8/2007 | Beaty et al. | | 382/145 |
| 2007/0183646 A1 * | 8/2007 | Beaty et al. | | 382/145 |
| 2009/0080764 A1 * | 3/2009 | Srinivasan et al. | | 382/150 |
| 2009/0180679 A1 * | 7/2009 | Hackney et al. | | 382/141 |
| 2012/0205296 A1 * | 8/2012 | Malek et al. | | 209/552 |
| 2013/0028504 A1 * | 1/2013 | Malek et al. | | 382/141 |

* cited by examiner

METHOD AND APPARATUS FOR 3-DIMENSIONAL VISION AND INSPECTION OF BALL AND LIKE PROTRUSIONS OF ELECTRONIC COMPONENTS

BACKGROUND

1. Field of the Disclosure

This disclosure relates to a method for inspecting objects in 3-dimensional vision, including inspecting electronic components which features' texture may require inspection that is detailed to a sub-pixel scale. An apparatus implementing such method is also disclosed.

2. Discussion of the Background Art

In a high-precision manufacturing environment where high volume of precision small objects are made, such as microelectronics fabrication and packaging of components, it is often necessary for each of the completed object such as a microelectronic package to be inspected for quality control purposes. Due to the large volume, such inspection has to be automated and due to the inspection involving examining specific critical feature of the package, such as co-planarity of the contact elements in the form of balls in a ball grid array (BGA) device, 3-dimensional vision is required.

Some vision systems use a single axial camera with a plurality of reflective surfaces to pick up different views of the object to be integrated in a single image such as that disclosed in U.S. Pat. No. 6,055,054 (Beaty, et al.), WO01/04567 and US-2002/37098. Normally, an algorithm in the form of software is used to process the different reflected views of the object to be integrated into a single image to be inspected.

Some other vision systems use at least two cameras such as that disclosed in U.S. Pat. No. 6,778,282 (ICOS Vision Systems), U.S. Pat. No. 6,064,756 and U.S. Pat. No. 6,064,757 (both by Beaty, et al.). These vision systems generally employ a first camera to capture an incident view of the object and a second camera to take a second view from another angle either directly or indirectly via reflective surfaces.

The present method for 3-dimensional vision inspection makes use of certain functions of Halcon™ Imaging Processing Library (version 7.1) by MVTec Software GmbH of München, Germany. Halcon™ user manual on 3-dimensional vision system entitled *Machine Vision in World Coordinates* which, along with other relevant Halcon™ publications, are incorporated herein by reference.

The stereoscopic camera system comprises two cameras trained on the same object from different positions. With a pair of cameras, a pair of image points from the projection of a point on the object may be captured. The image points are often referred to as "conjugate points" or "homologous points". By making use of interior parameters of both cameras and the relative pose of the second camera with respect to the first camera obtained during a prior calibration process, the distance of the said object point from the stereoscopic camera system can be determined.

A simplified configuration of two parallel-trained cameras with identical interior parameters may be shown in FIG. 1 (Prior Art). The basis, i.e. the straight line connecting the two optical centres of the two cameras, may be assumed to be coincident with the x-axis of the first camera. Then, the image to coordinates, $u_1$ and $u_2$, of the projections of the point P ($x^c$, $z^c$) into the image planes may be expressed as follows:

$$u_1 = f \frac{x_c}{z_c}$$

$$u_2 = f \frac{x^c - b}{z^c}$$

where f is the focal length and b the length of the basis. The difference between the two image locations of the conjugate points is called the disparity d, which may be calculated as follows:

$$d = (u_1 - u_2) = \frac{f \cdot b}{z^c}$$

Given the camera parameters and the image coordinates of two conjugate points, the $z^c$ coordinate of the corresponding object point P, i.e. the distance from the stereo camera system, can be computed from the following equation:

$$z^c = \frac{f \cdot b}{d}$$

It should be noted that the interior camera parameters of both cameras and the relative pose of the second camera in relation to the first camera are necessary to determine the distance of P from the stereo camera system.

Two basic operations that need to be solved for conventional stereo vision are:

(1)—Determination of the interior parameters of both cameras and the relative pose between them during initial set-up, and (2)—Determination of a pair of conjugate points for each object point of interest in stereo image pair captured during inspection to compute the distance of said object points from the stereoscopic camera system.

The first operation involves calibration of the stereo camera system whereby a calibration plate is placed such that it is completely within both of the field of views of the stereo cameras. With Halcon™ Imaging Processing Library, the calibration of both images may be carried out simultaneously with the operator termed as "binocular calibration" [see section 7.3, page 94 of *Machine Vision in World Coordinates*, Edition 2, Halcon™ 7.1.0, published July 2005]. After a successful calibration, a virtual stereo camera system called rectified stereo camera system, of which the rectified coordinate system is with respect to the first camera, will be constructed.

As the accuracy of the 3-dimensional image representation is influenced by the manner in which the cameras are placed, it is important that neither the interior camera parameters (e.g., the focal length) nor the relative pose (e.g., the distance and orientation between the two cameras) of the two cameras should change during the calibration process or between the calibration process, as well as during the ensuing application of the calibrated stereo camera system. It is therefore advisable to mount the two cameras on to a stable platform.

The second operation involves what is called "stereo matching process", which in Halcon™ processing involves invoking the operators "binocular disparity" or "binocular distance" [see section 7.4, page 97, op. cit.] which process the necessary calculations to obtain world coordinates from the stereo images. In Halcon™ processing, two image points from a stereo image pair captured from the same object point are referred to as conjugate points. From the principle of stereovision, the difference between image locations of the conjugate points, which is called the "disparity", can be used to compute the distance of an object point from the rectified stereo camera system.

The Halcon™ Library provides individual functions to compute disparity or distance of the entire overlapping region of the stereo image pair. These functions must first carry out matching operation to establish conjugate points for all image points within the overlapping region of stereo image pair before disparity or distance profile of the region can be computed. The stereo image pair must first be rectified, based on information gathered from calibration, to align their overall Y image coordinate. Thus the ensuing matching process is mainly to find out the difference of conjugate points in X image coordinate. There are 3 different methods, namely "summed absolute difference", "summed squared differences" and "normalized cross correlation", available for the matching function and all 3 are based on comparison of gray-level pattern within a small matching window. To obtain accurate results, the surface of the object must have enough textural information to be captured.

Unfortunately, this approach is not useful when determining the distance to a small feature having varying surface curvature (hence varying distance) such as a contact solder ball tip of a ball grid array semiconductor package. Using Halcon™ matching methods would be cumbersome and inaccurate as the ball surface is void of textural features and is therefore not suitable for Halcon™ matching methods.

Nevertheless, Halcon™ methodology also provides functions to compute distance from disparity of conjugate points or distance from the conjugate points directly whereby the conjugate points are to be determined by the user. It should be noted that conjugate points can be taken as rectified image coordinates or original image coordinates.

We are now able to detect the conjugate points of the ball tips using the present method and yet be able to compute the distance of every ball tip from rectified stereo cameras using Halcon functions. The process may be more readily understood from the following disclosure.

SUMMARY OF DISCLOSURE

The present disclosure concerns "a method for 3-dimensional vision inspection of objects, including microelectronic components having protrusions as features to be inspected", wherein the protrusions have non-planar surfaces and/or surface curvatures and have no fine textures, such as the tips of pins or balls. In the general embodiment, the method comprises the steps of:

(a) providing a stereo camera system comprising at least a pair of cameras arranged in a stereovision configuration, wherein the first camera captures a side view of said object, and the second camera captures an opposite side view of said object;

(b) calibrating said stereo camera system to determine the interior parameters of said respective cameras and exterior parameters, or relative pose including position and orientation, of the second camera with respect to the first camera;

(c) forming a rectified stereo camera system with a rectified camera coordinate system from the parameters of said stereo camera system determined above, and determining the interior parameters of said respective rectified cameras and exterior parameters, or relative pose including position and orientation, of the second rectified camera with respect to the first rectified camera, wherein, the optical centers of the rectified cameras are the same as those of said stereo cameras, but the rectified cameras are rotated such that both rectified cameras are in parallel and their X axes are collinear, and the orientation of the rectified cameras is defined by the cross product of line connecting the optical centers of said stereo cameras, and line of intersection of the image planes of said stereo cameras, and both rectified cameras have the same focal length;

(d) using said stereo camera system to capture a pair of images of said object comprising two side views of surface curvature of each of the protrusions of said object;

(e) rectifying each image to produce a pair of rectified images as captured by said rectified stereo camera system, wherein, the rectified images are on the image planes of the rectified cameras;

(f) determining a pair of conjugate points for the tip of each protrusion in the rectified images; and (g) determining the location of each protrusion in the rectified coordinate system based on said pair of conjugate points and said interior and exterior parameters of said rectified stereo camera system.

In one preferred embodiment, the interior parameters include focal length, optics center, distortion coefficients, and sensor cell size and the exterior parameters or the relative pose includes roll angle, tilt angle, pan angle, and translation along X axis, Y axis, and Z axis respectively of one camera with respect to the other camera.

One preferred embodiment of the method further includes a step (h), i.e. calculating the co-planarity of the protrusions based on the locations of the protrusions by forming a seating plane using a standard best-fit plane algorithm.

In one aspect of the disclosure, the protrusion height is calculated by (i) approximating a plane, based on the locations of the protrusions having good co-planarity values; (ii) shifting said plane by the amount of nominal protrusion height to form the substrate plane; and (iii) taking the height of the protrusion as the perpendicular distance of said protrusion to the substrate plane.

In a preferred embodiment, the calibration in step (b) is achieved with the use of a calibration grid.

In another preferred embodiment determination of the conjugate points of each protrusion in the step (f) includes: (i) locating in each rectified image, the edges of the object to draw up the boundaries of the object; and (ii) performing standard blob analysis to locate the gross position of each protrusion. Preferably, the step (f) further includes: (iii) projecting two edge-detecting windows onto each protrusion to locate its top and bottom edges up to sub-pixel accuracy; (iv) projecting a third edge-detecting window from a central vertical position of the protrusion to detect the left edge of the protrusion in the rectified right image and the right edge of the protrusion in the rectified left image up to sub-pixel accuracy; and (v) assigning conjugate points to be the right edge detected in the rectified left image and the left edge detected in the rectified right image of the protrusion.

In yet another embodiment of the method, the step (g) further includes: determining the location of the protrusion in the rectified camera coordinate system utilizing the positions of the conjugate points and the interior parameters and exterior parameters, or relative pose of the rectified cameras computed during calibration; or includes (i) calculating disparity of the protrusion to be the difference between the positions of the conjugate points; and (ii) determining the location of the protrusion in the rectified camera coordinate system utilizing the positions of one of the conjugate points, the disparity and, the interior parameters and exterior parameters, or relative pose of the rectified cameras computed during calibration.

In yet another embodiment of the method, computation of the height of the protrusion in the step (i) includes: (i) approximating a plane base on the locations of the protrusions whose co-planarity is smaller than a certain threshold (good co-planarity); (ii) shifting the plane by the amount of nominal protrusion height to form a substrate plane; and (iii) taking the height of the protrusion as the perpendicular distance of the protrusion to the substrate plane.

Preferably, the protrusion to be inspected in our method has at least one of a round edge or ball tip, including pins of a pin grid array (PGA) package, balls of ball grid array (BGA), and like microelectronic packages.

In another aspect of the disclosure, an apparatus is provided for 3-dimensional vision inspection of non-planar objects, including microelectronic components, wherein any one of the preceding methods is enabled for calibration and/or measurement purposes. The apparatus comprises:
(a) at least a pair of cameras arranged in a stereovision configuration, wherein the first camera captures a side view of said object, and the second camera captures and opposite side view of said object;
(b) a pair of reflective surfaces for reflecting the object into each of said cameras respectively; and
(c) means for mounting said object in the field of view of said cameras; wherein said object has a plurality of co-planar protrusions on at least one surface or substrate.

Preferably, the object to be inspected is placed within a ring of light source and is illuminated thereby. Preferably still, the light source comprises a plurality of light-emitting diodes (LED) with their light beam positioned at about an inclination of 25° towards the object to be inspected. A background light source may preferably be further provided.

As a preferred embodiment, the cameras are further connected to a data processing means via a frame grabber, or a high-speed data transfer bus including an IEEE-1394 bus (also known as "Firewire"). Preferably, the data processing means is a computer capable of running at least a program for calibrating, rectifying and processing captured images.

In an alternative embodiment, the apparatus may further include a third camera. Preferably, the third camera is placed in between the pair of first two cameras and is configured for inspecting another type of feature of the object, or another type of object.

In another alternative embodiment, a calibration reticle for having its image captured for calibration process is provided removably mounted. The reflective surfaces are preferably positioned at an inclination of about 22.5° is from parallel axis towards the object to be inspected so that images of said object are reflected at parallel into the cameras.

These and other advantages of the disclosure may be better understood with reference to the accompanying drawings and the detailed description in the following.

BRIEF DESCRIPTION OF THE DRAWINGS

The present disclosure will now be described in detail with reference to the accompanying drawings that follows, wherein specific embodiments are described as non-limiting examples or illustrations of the workings of the disclosure, in which.

DETAILED DESCRIPTION OF THE PREFERRED EMBODIMENT

Figure 1:
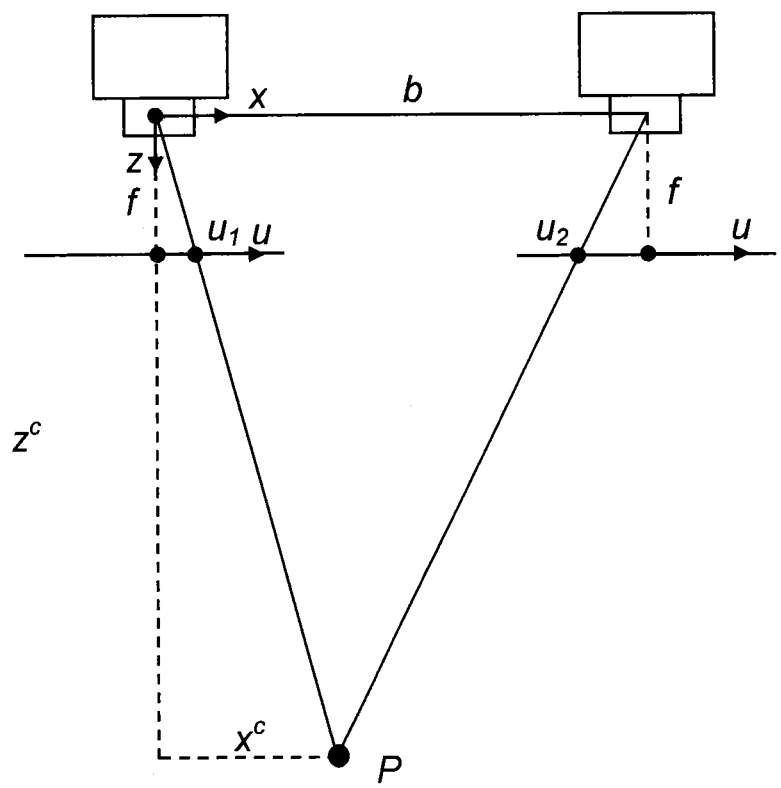
FIG. 1 (Prior Art) shows a simplified configuration of two parallel-trained single-dimension cameras with identical interior parameters employed in a conventional imaging system.
Figure 2:
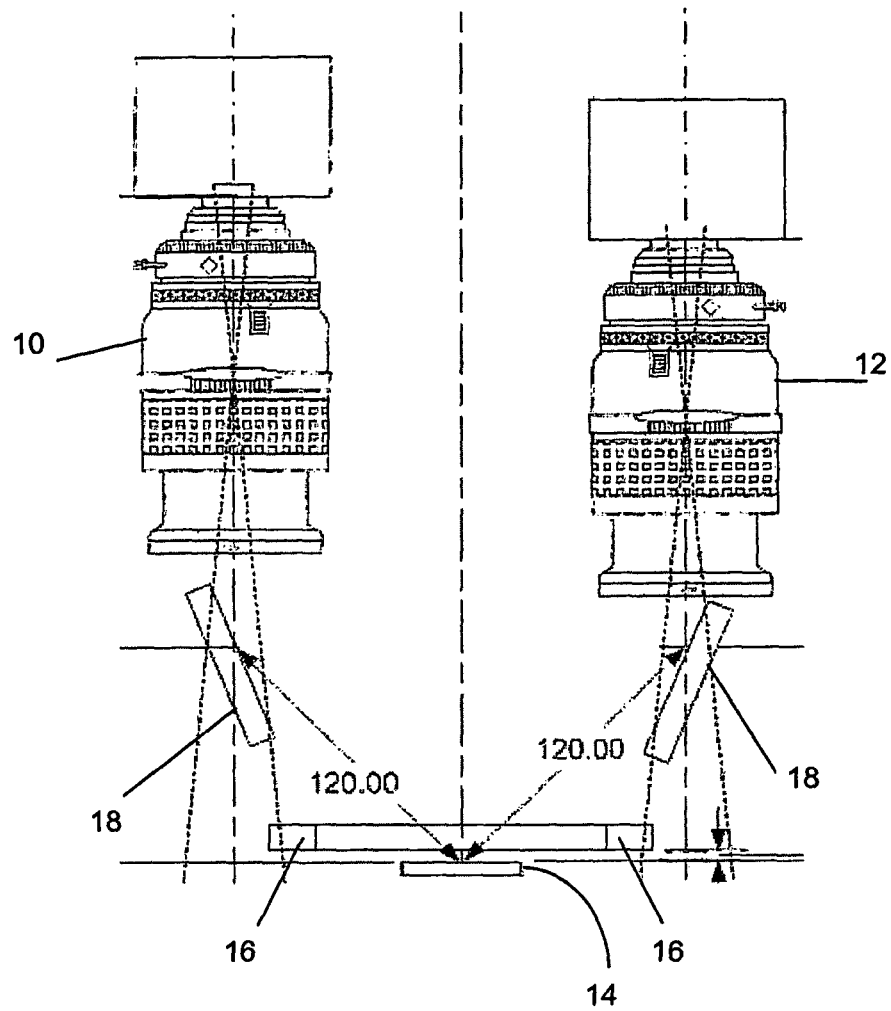
FIG. 2 shows a basic embodiment of an apparatus in elevation view which enables the method according to the disclosure.

In the general embodiment of the invention, the method for 3-dimensional vision inspection may be implemented by a stereo configuration or arrangement of a pair of cameras (10, 12) and other elements such as the lighting elements including the ring light (16) and the reflective surfaces or mirrors (18) as shown in FIG. 2 in an elevation view.

The novel method for 3-dimensional vision inspection covers objects (14) such as micro-electronic components having features to be inspected which may include input-output contact points protruding from the package as non-planar surfaces and/or surface curvatures, such as pins and balls of microelectronic packages, including pin grid array (PGA) packages, ball grid array (BGA) and like packages.

The method includes the steps of:
(a) providing a stereo camera system comprising at least a pair of cameras arranged in a stereovision configuration, wherein the first camera captures a side view of said object, and the second camera captures an opposite side view of said object;
(b) calibrating said stereo camera system to determine the interior parameters of said respective cameras and exterior parameters, or relative pose including position and orientation, of the second camera with respect to first camera;
(c) forming a rectified stereo camera system with a rectified coordinate system from the parameters of said stereo camera system determined above, and determining the interior parameters of said respective rectified cameras and exterior parameters, or relative pose including position and orientation, of the second rectified camera with respect to the first rectified camera, wherein, the optical centers of the rectified cameras are the same as those of said stereo cameras, but the rectified cameras are rotated such that both rectified cameras are in parallel and their X axes are collinear, and the orientation of the rectified cameras is defined by the cross product of line connecting the optical centers of said stereo cameras, and line of intersection of the image planes of said stereo cameras, and both rectified cameras have the same focal length;
(d) using said stereo camera system to capture a pair of images of said object comprising two side views of surface curvature of each of the protrusions of said object;
(e) rectifying said pair of images to produce a pair of rectified images as captured by said rectified stereo camera system, wherein, the rectified images are on the image planes of the rectified cameras;

(f) determining a pair of conjugate points for the tip of each protrusion in the rectified images; and (g) determining the location of each protrusion in the rectified camera coordinate system based on said pair of conjugate points and said interior and exterior parameters of said rectified stereo camera system for 3-dimensional vision inspection of said objects.

The calibration step (b) above may be achieved with the use of a calibration grid.

Figure 3:
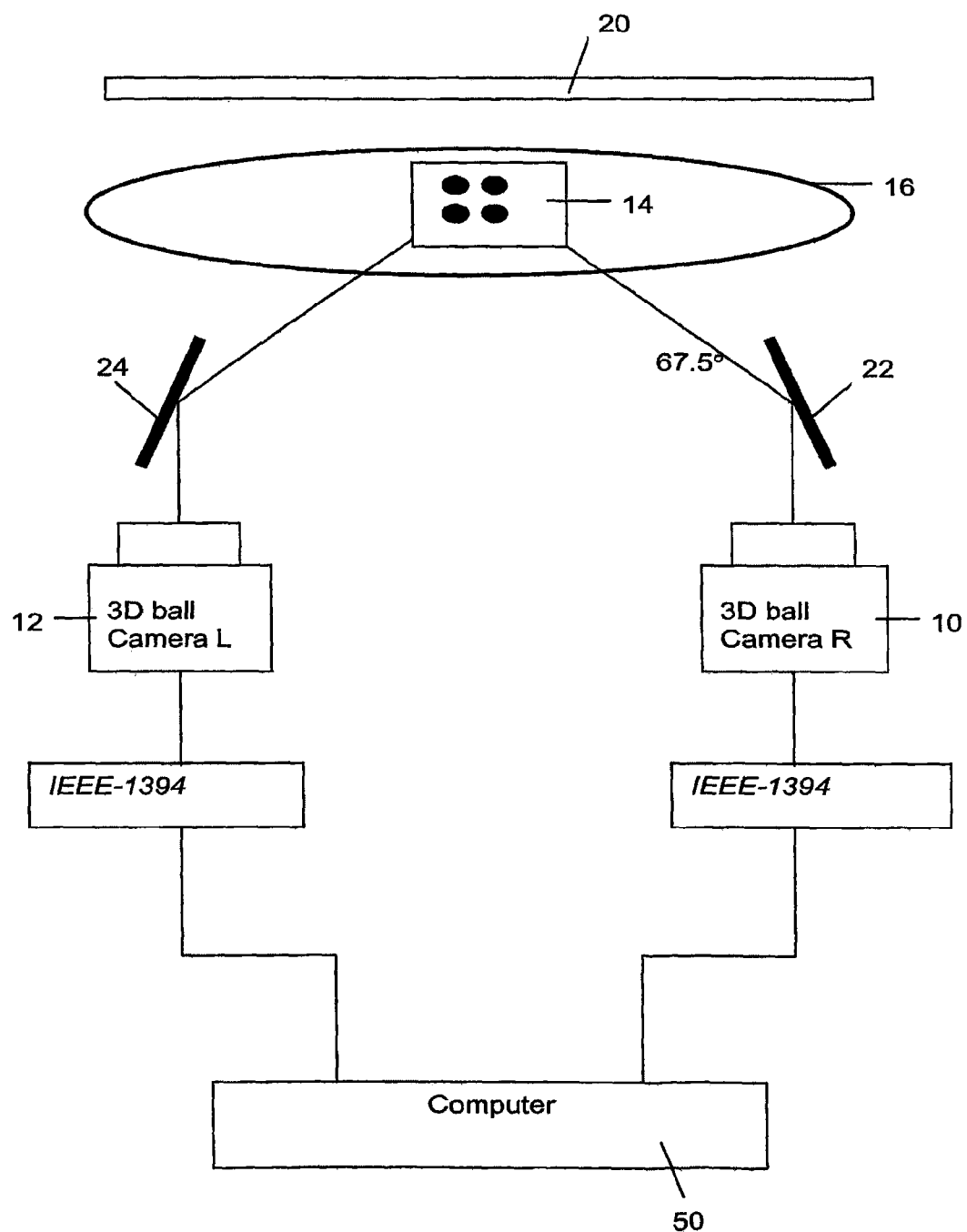
FIG. 3 shows a calibration grid in form of a square block for use in calibration steps of our disclosure.

The calibration grid may be provided as a removably mountable block to be captured by the stereoscopic camera system. The calibration grid is preferably a rectangular board provided with an array of precision dots within a rectangular border, as shown in FIG. 3. As an exemplary calibration process, the calibration grid may be captured at 20 different positions with different orientations within the field of view of the cameras. At least 10 images may then be selected for the calibration process.

During the calibration process, the image pairs are read in sequence to obtain the locations of the dots within the border. As the precise spatial relationship among the dots are known, Halcon™ functions may be used to compute the interior camera parameters and the spatial relationship between the two cameras. The interior camera parameters include the focus length, the distortion coefficients, the optics centre, the sensor cell size of individual cameras. The spatial relationship between the two cameras is the relative pose including the position and the orientation of one camera in relation to the other camera. The relative pose, also called 3D pose, includes translations along 3 axes respectively and rotations around 3 axes respectively. With this information, a virtual stereo camera system called "rectified stereo camera system" in which the "rectified coordinate system" is determined with respect to the first camera can be established according to the Halcon™ method. The optical centers of the rectified cameras are the same as those of the stereo cameras, but the rectified cameras are rotated such that they are in parallel and their X axes are collinear. The orientation of the image planes of the rectified cameras is defined by the cross product of line connecting the optical centers of the stereo cameras and line of intersection of the image planes of the stereo cameras. In addition, both rectified cameras have the same focal length. The focal length of the rectified cameras and the relative pose between the rectified cameras can be also obtained in the process.

It should be explained here that the term "relative pose" is used in this specification to mean "exterior parameters" of the cameras or 3D camera's positions relative to one another as well as to the object to be examined. The "relative pose" term may also be taken to mean "3D poses" employed in Halcon™ methodology. In Halcon™, 3D poses means representation of a rigid transformation with 6 parameters, i.e. 3 for rotation and 3 for translation (Rot1, Rot2, Rot3, TransX, TransY, TransZ). The principle of poses is that transformation around even an arbitrary axis can still be represented by a sequence of 3 rotations around the X, Y and Z axes of a coordinate system.

Theoretically, after binocular calibration, the locations of everything in front of the stereoscopic camera system can be determined. Even though the relative pose (exterior parameters) derived from binocular calibration has a so-called "measurement plane" in it (world coordinate of z=0), it is not important in 3D measurement. Practically, the locations of all object points falling within focusing range of the stereoscopic camera system can be detected properly using the calibration information and the conjugate points of the object point. Measurement plane is more relevant for 2D measurement whereby the object is planar and always physically situated on the measurement plane.

Before detection of the conjugate points, the stereo images are rectified to produce the rectified stereo images. The rectified stereo images are on the image planes of the rectified cameras and can be thought of as being acquired by the rectified stereo camera system.

The determination of conjugate points of each protrusion of step (f) may preferably include (i) locating in each rectified image, the edges of the object to draw up the boundaries of the object; and (ii) performing standard blob analysis to locate the gross position of each protrusion. Step (f) further includes (iii) projecting two edge-detecting windows onto each protrusion to locate its top and bottom edges up to sub-pixel accuracy; (iv) projecting a third edge-detecting window from a central vertical position of the protrusion to detect the left edge of the protrusion in right image and the right edge of the protrusion in the left image up to sub-pixel accuracy; and (v) assigning conjugate points to be the right and left edges of the protrusion.

Detection of location of each protrusion of step (g) includes (i) determining the location of the protrusion in the rectified camera coordinate system utilizing the positions of the conjugate points and the interior parameters and the exterior parameters or the relative pose of the rectified cameras computed during calibration; or (ii) calculating disparity of the protrusion to be the difference between the positions of the conjugate points. (iii) determining the location of the protrusion in the rectified camera system utilizing the position of one of the conjugate point, the disparity and the interior parameters and the exterior parameters or the relative pose of the rectified cameras computed during calibration.

Preferably, the method further includes the step of calculating the co-planarity of the protrusions based on the locations of all the protrusions by is forming a seating plane using standard best-fit plane algorithm.

The method for 3-dimensional vision as described above may preferably further include the calculation of the height of protrusion by the following steps:

(i) approximating a plane based on the locations of the protrusions having good co-planarity values, wherein good co-planarity means co-planarity is smaller than a certain threshold;

(ii) shifting said plane by the amount of nominal protrusion height to form the substrate plane; and (iii) taking the height of a protrusion as the perpendicular distance of said protrusion to the substrate plane.

As shown in FIG. 2, the configuration of an apparatus which enables the calibration and/or measurement step outlined above may comprise of:

(a) at least a pair of cameras arranged in a stereovision configuration, wherein the first camera captures a side view of said object, and the second camera captures an opposite side view of said object;

(b) a pair of reflective surfaces for reflecting the object to be inspected into each of cameras;

(c) means for mounting said object to be inspected in the field of view of the stereo camera system;

wherein said object has a plurality of co-planar protrusions on at least one surface or substrate.

The camera may cover still cameras or video cameras. The term "at least a pair" covers two or more camera wherein at least two of the cameras are for stereoscopic vision while the third and subsequent cameras are optional and may or may not relate to inspecting ball-like protrusions from an object to be inspected.

Reflective surfaces may be provided at an inclination of about 22.5° from parallel axis towards the object to be inspected so that images of said object are reflected at parallel into the image capturing devices.

Figure 6:
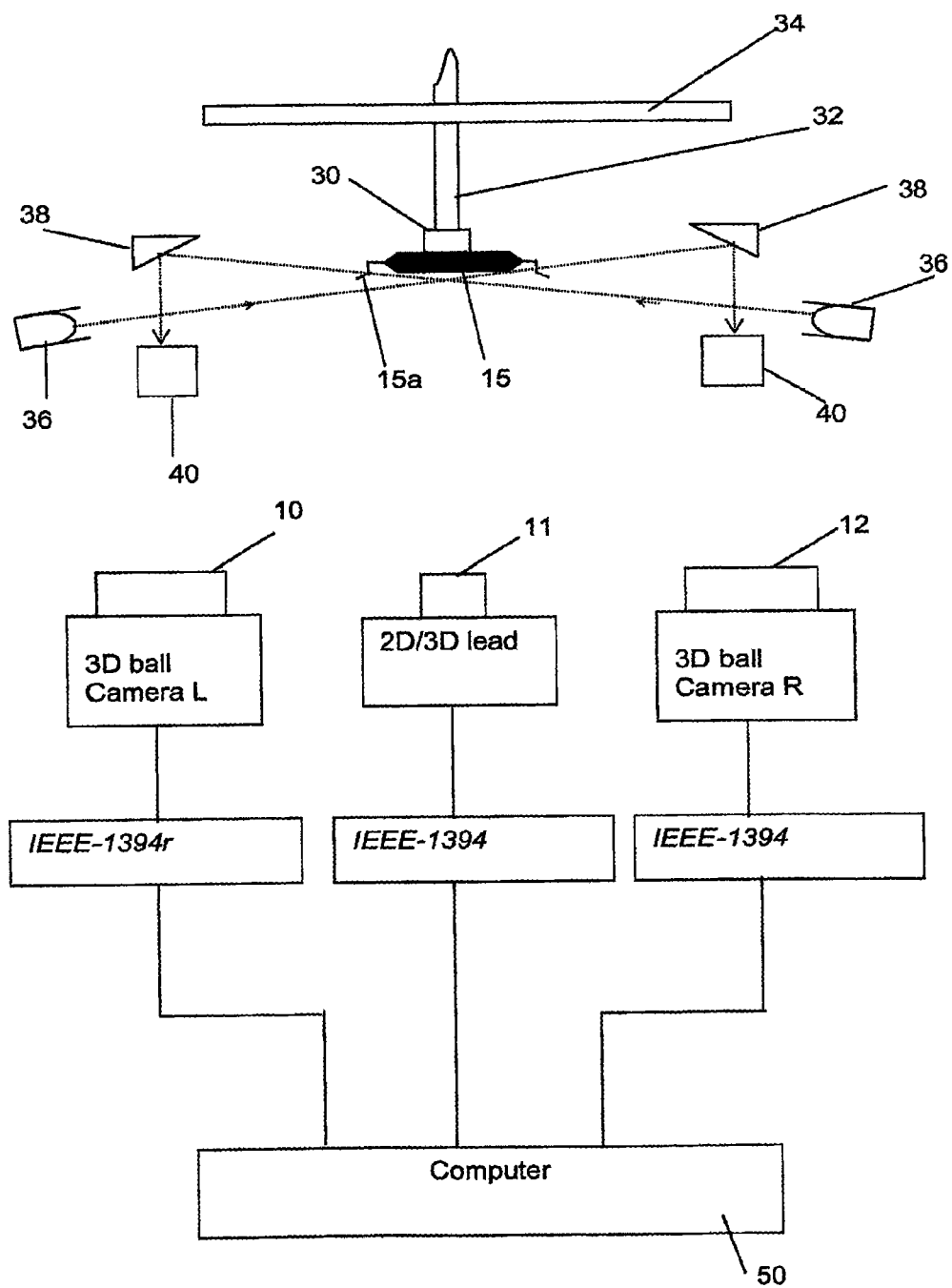
FIG. 6 shows a second embodiment of an apparatus in schematic representation, which includes a third camera, a light source and mirrors for 2-dimension/3-dimension lead imaging.

The object to be inspected is preferably placed within and is illuminated by a ring of light source. The light source ring comprises a plurality of light-emitting diodes (LED) with their light beam positioned at about an inclination of 25° towards the object to be inspected. Preferably, a background light source is further provided. The spatial arrangement of the cameras and lighting means may be varied according to the features of the object to be captured and processed. For example, as shown in FIG. 6, the object (14) which image is to be captured, may be placed within ring light (16) to provide peripheral illumination to the object (14). A backlight (20) may additionally be provided to provide background illumination.

Figure 4:
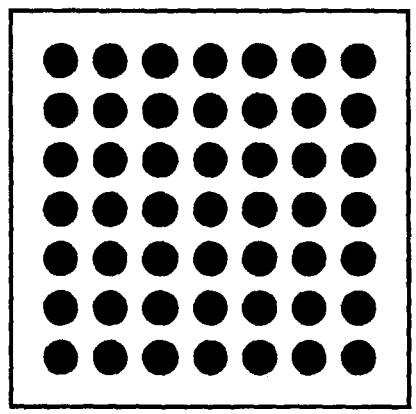
FIG. 4 shows an embodiment of an apparatus in schematic representation, which includes a back light source for calibration purposes.

In one preferred embodiment, as shown in FIG. 4, the cameras are connected to a data processing means via a high-speed data transfer bus is including an IEEE-1394 bus (also known as "Firewire"). Data processing means in the form of a computer capable of running at least a program for calibrating, rectifying and processing captured images is provided.

The images reflected from the object (14) need not be captured directly by the cameras (10, 12). In fact, as the object size is likely to be a small microchip as is the common form factor of microelectronic packages today, it would be difficult to mount the cameras (10, 12) in parallel to capture the images directly. It would be more practical to have the images captured by the cameras (10, 12) indirectly, i.e. via reflective surfaces or mirrors (22, 24) so that the cameras (10, 12) may be placed apart but still parallel to each other. Preferably, the mirrors (22, 24) are placed at about 22.5° inclination from the parallel axis to the object (or 67.5° inclination from the plane or field of vision upon which the object to be captured is placed).

Figure 5:
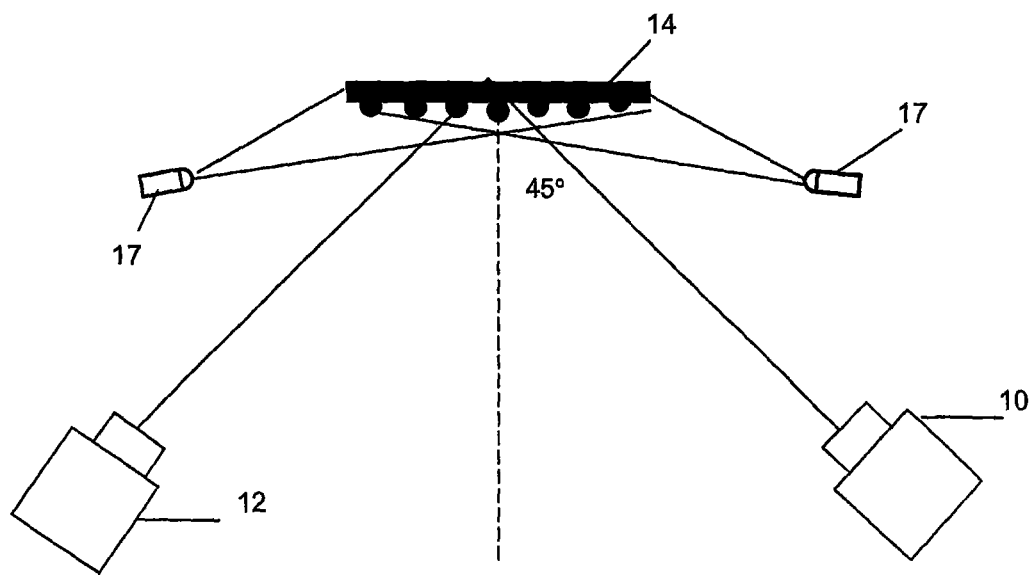
FIG. 5 shows one embodiment of an apparatus in schematic representation, for inspection purposes.

FIG. 5 shows an alternative arrangement wherein the object to be inspected (14) is still placed within a ring light comprising LED elements (17). In this arrangement, the cameras are positioned at about 45° on each side from the incidental axis of the object (14).

FIG. 6 shows another alternative embodiment wherein the object to be examined is a leaded microelectronic package (15) wherein is featured with leads (15*a*) protruding from the sides of the package. The package (15) is shown picked up by a vacuum wand comprising a pick head (30) and pick arm (32). A backlight or reflector (34) may be provided so that the package (15) may be illuminated from the background. Bar lights (36) are shown provided to illuminate the sides of the package (15), particularly at the peripheral parts where the leads protrude from the package body. Reflective surfaces or mirrors (38) may be provided at the same level as the leads to reflect the images to cameras (10, 12). Preferably, the images are transmitted through optical elements (40), including non-linear optical elements, filters, etc. to enhance the contrast of the images.

It is to be noted that a third camera (11) may optionally be provided in the middle or between the two cameras (10, 12) to enable the images from the bottom of the packages be captured as a whole to be compared or rectified against the separate peripheral images of the leads on each side of the package (15). As with the pair of cameras (10, 12), this third camera (11) may be connected via a high-speed data transfer bus such as Firewire connection (or IEEE-1394 bus). Data processing means in the form of a computer (50) running a program for calibrating, rectifying and processing captured images may be optionally provided.

Figure 7:
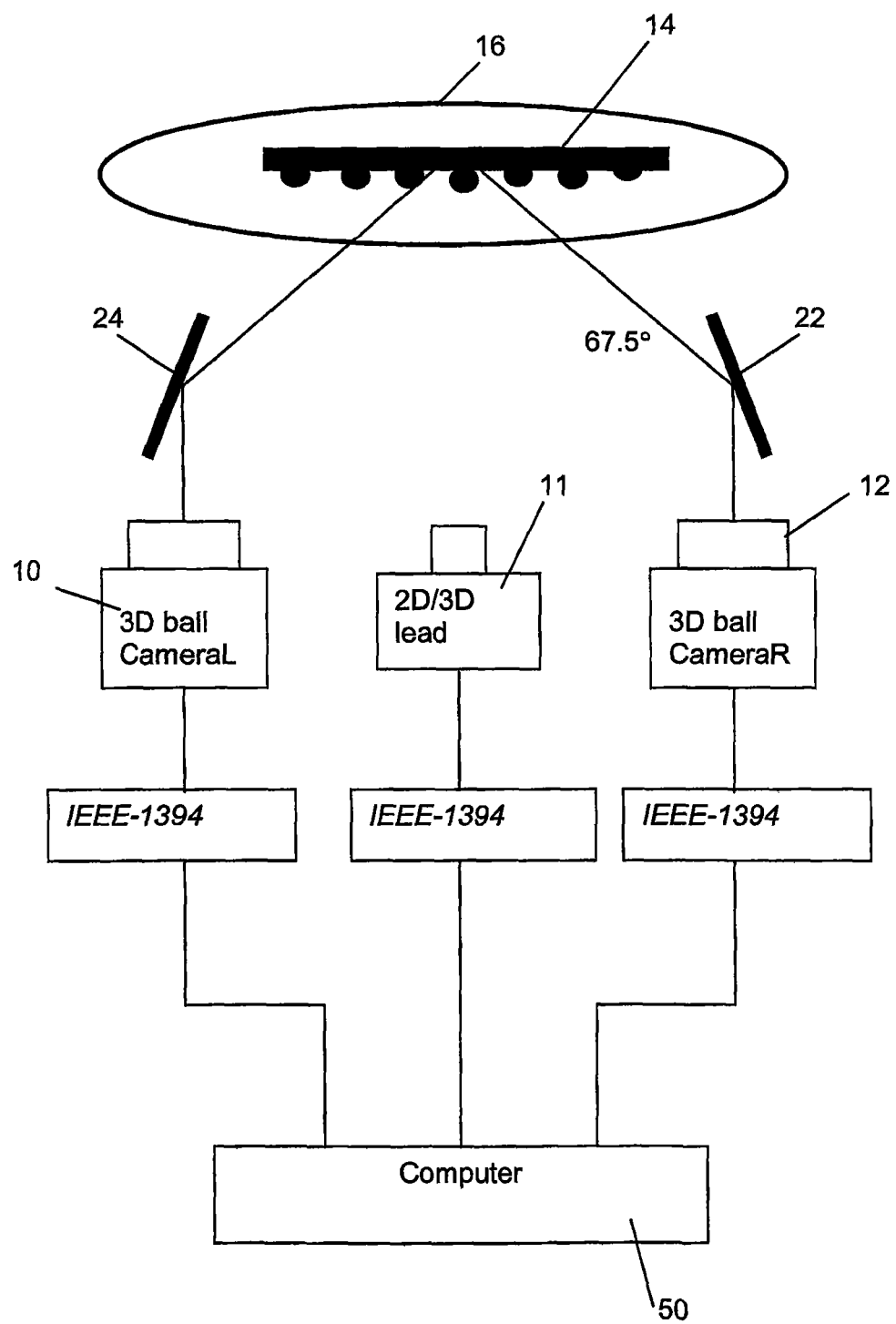
FIG. 7 shows a third embodiment of an apparatus in schematic representation, for inspection purposes.
Figure 8:
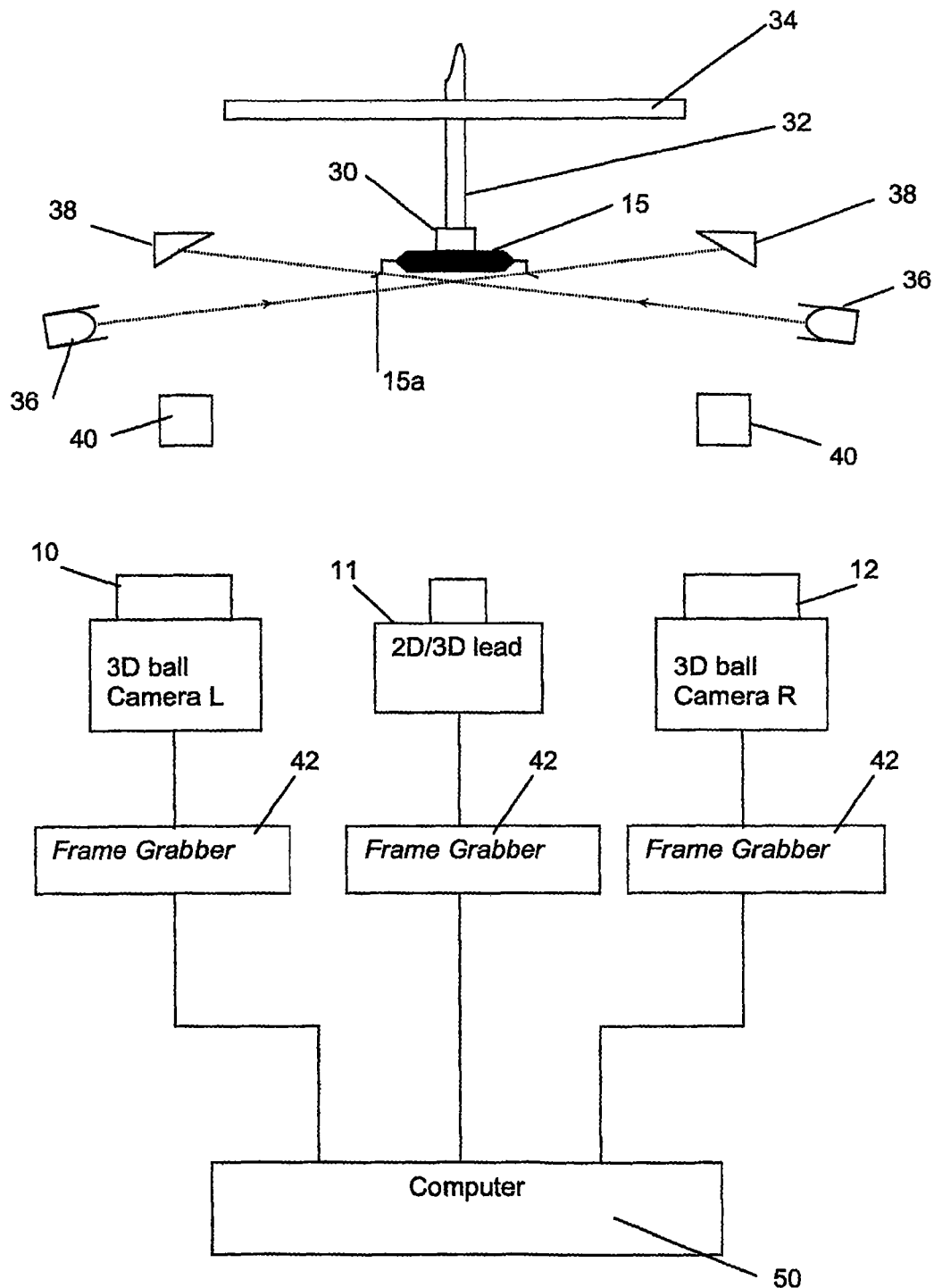
FIG. 8 shows a fourth embodiment of an apparatus in schematic representation, for inspection purposes.
Figure 9:
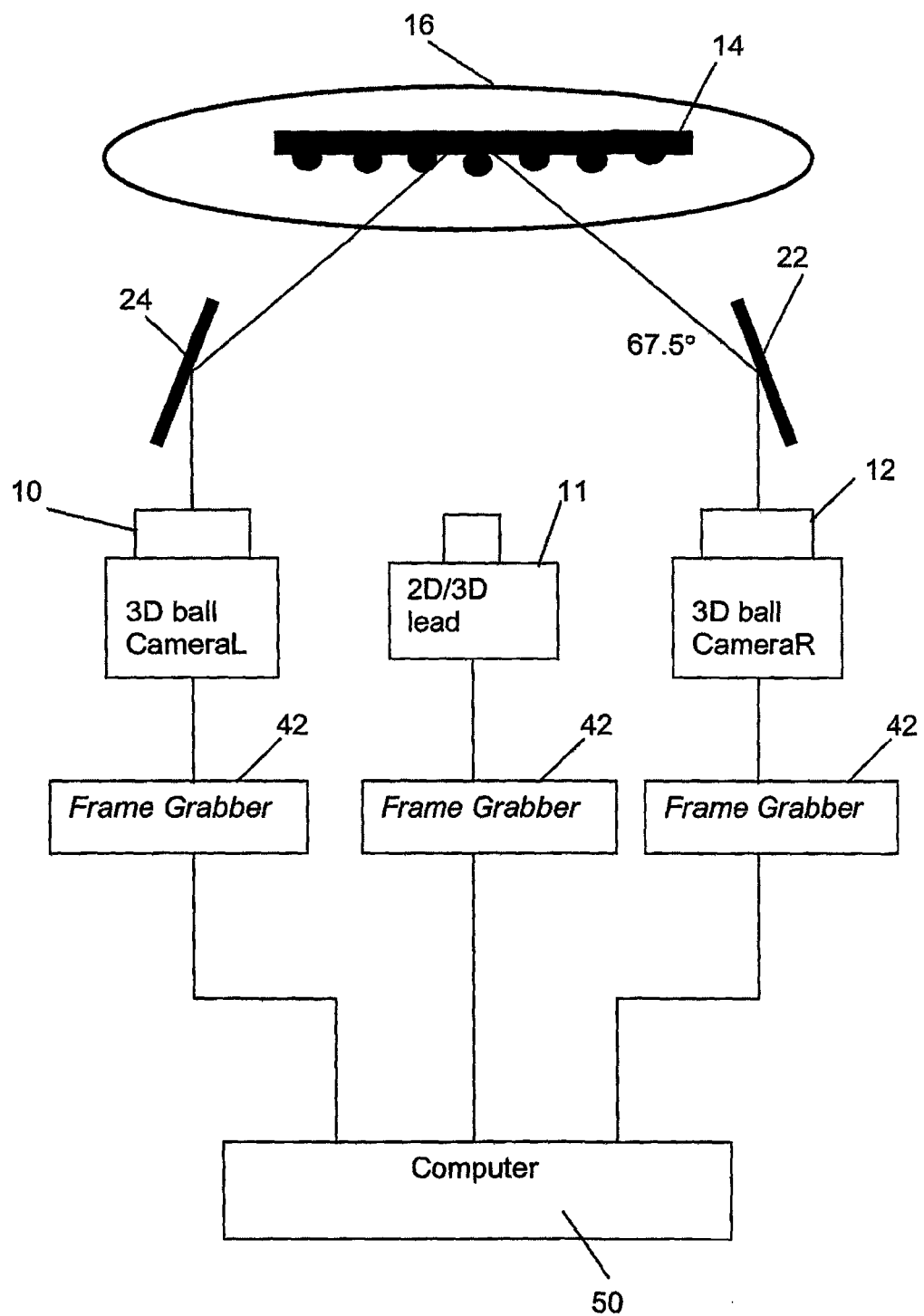
FIG. 9 shows a fifth embodiment of an apparatus in schematic representation, for inspection purposes.

FIG. 7 shows a modification of the arrangement of FIG. 6 wherein the third camera (11) is similarly provided as an optional configuration. Instead of using high speed data transfer bus and still cameras, video cameras may be used for fast throughput examination of the microelectronic packages or, other objects to be examined, wherein frame grabbers (42) (or other external devices) may be used in line with each of the video cameras so that the video images may be digitized for processing in the computer (50), as shown in FIGS. 8 and 9.

Certain parallelization processes or parallel processing of images in Halcon™ image functions and operators realized by multi-threaded programming and multi-core processing means may be used to speed up processing time. Other third party image processing algorithms, including frame grabber interfaces, may also be used integrally with Halcon™ in speeding up certain processes of our novel method described herein. Such modifications, extension or adaptations are not to be considered as departures from the scope of the present disclosure as defined in the following claims.

What is claimed is:

1. A method for 3-dimensional vision inspection of objects, including microelectronic components, having protrusions as features to be inspected, wherein said protrusions having non-planar surfaces and/or surface curvatures, said method comprising the steps of:
   (a) providing a stereo camera system comprising at least a pair of cameras arranged in a stereovision configuration, wherein the first camera captures a side view of said object, and the second camera captures an opposite side view of said object;
   (b) calibrating said stereo camera system to determine the interior parameters of said respective cameras and exterior parameters, or relative pose including position and orientation, of the second camera with respect to the first camera, wherein the interior parameters include focal length, optics center, distortion coefficients, and sensor cell size and the exterior parameters or the relative pose includes roll angle, tilt angle, pan angle, and translation along X axis, Y axis, and Z axis respectively of one camera with respect to the other camera;
   (c) forming a rectified stereo camera system with a rectified camera coordinate system from the parameters of said real stereo camera system determined above, and determining the interior parameters of said respective rectified cameras and exterior parameters, or relative pose including position and orientation, of the second rectified camera with respect to the first rectified camera, wherein, the optical centers of the rectified cameras are the same as those of said stereo cameras, but the rectified cameras are rotated such that both rectified cameras are in parallel and their X axes are collinear, and the orientation of the rectified cameras is defined by the cross product of line connecting the optical centers of said stereo cameras, and line of intersection of the image planes of said stereo cameras, and both rectified cameras have the same focal length;
   (d) using said stereo camera system to capture a pair of images of said object comprising two side views of surface curvatures of each of the protrusions of said object;
   (e) rectifying said pair of images to produce a pair of rectified images as captured by said rectified stereo camera system, wherein, the rectified images are on the image planes of the rectified cameras;
   (f) determining a pair of conjugate points for the tip of each protrusion in the rectified images; and (g) determining the location of each protrusion, which include x, y, and z coordinates, in the rectified camera coordinate system based on said pair of conjugate points and said interior and exterior parameters of said rectified stereo camera system for 3-dimensional vision inspection of said objects.

2. The method for 3-dimensional vision inspection according to claim 1 further including the step of:
   (h) calculating the co-planarity of the protrusions based on the locations of the protrusions by forming a seating plane using a standard best-fit plane algorithm.

3. The method for 3-dimensional vision inspection according to claim 2 further including the step of:
   (i) calculating the height of each protrusion wherein a substrate plane is determined and the perpendicular distance of protrusion to the substrate plane is taken as the height of the protrusion.

4. The method for 3-dimensional vision inspection according to claim 3 wherein the height of the protrusion is calculated as follows:
   (i) approximating a plane, based on the locations of the protrusions having co-planarity values;
   (ii) shifting said plane by the amount of nominal protrusion height to form the substrate plane; and
   (iii) taking the height of the protrusion as the perpendicular distance of said protrusion to the substrate plane.

5. The method for 3-dimensional vision inspection according to claim 1 wherein the calibration step is-achieved with the use of a calibration grid.

6. The method for 3-dimensional vision inspection according to claim 1 wherein the conjugate points of each protrusion being determined in the step (f) includes
   (i) locating in each rectified image, the edges of the object to draw up the boundaries of the object; and
   (ii) performing standard blob analysis to locate the gross position of each protrusion.

7. The method for 3-dimensional vision inspection according to claim 6 wherein step (f) further includes
   (iii) projecting two edge-detecting windows onto each protrusion to locate its top and bottom edges up to sub-pixel accuracy;
   (iv) projecting a third edge-detecting window from a central vertical position of the protrusion to detect the left edge of the protrusion in the rectified right image and the right edge of the protrusion in the rectified left image up to sub-pixel accuracy; and
   (v) assigning conjugate points to be the right edge detected in the rectified left image and the left edge detected in the rectified right image of the protrusion.

8. The method for 3-dimensional vision inspection according to claim 1 wherein step (g) further includes
   (i) determining the location of the protrusion in the rectified camera coordinate system utilizing the positions of the conjugate points and the interior parameters and exterior parameters, or relative pose of the rectified cameras computed during calibration; or
   (ii) calculating disparity of the protrusion to be the difference between the positions of the conjugate points; and
   (iii) determining the location of the protrusion in the rectified camera coordinate system utilizing the position of one of the conjugate points, the disparity, and the interior parameters and exterior parameters, or relative pose of the rectified cameras computed during calibration.

9. An apparatus for 3-dimensional vision inspection of non-planar objects, including microelectronic components, wherein the method according to claim 1 is enabled for calibration and/or measurement purposes, said apparatus comprising:
   (a) at least a pair of cameras arranged in a stereovision configuration, wherein the first camera captures a side view of said object, and the second camera captures an opposite side view of said object;
   (b) a pair of reflective surfaces for reflecting said object into each of said cameras respectively; and
   (c) means for mounting said object in the field of view of said cameras;
   wherein said object has a plurality of co-planar protrusions on at least one surface or substrate.

10. The apparatus for 3-dimensional vision inspection according to claim 9 wherein the object to be inspected is placed within a ring of light source and is illuminated thereby.

11. The apparatus for 3-dimensional vision inspection according to claim 10 wherein the light source comprises a plurality of light-emitting diodes (LED) with their light beam positioned at an inclination of 25° towards the object to be inspected.

12. The apparatus for 3-dimensional vision inspection according to claim 11 wherein a background light source is further provided.

13. The apparatus for 3-dimensional vision inspection according to claim 12 wherein the cameras are connected to a data processor via a frame grabber or a high-speed data transfer bus including an IEEE-1394 bus (also known as "Firewire").

14. The apparatus for 3-dimensional vision inspection according to claim 13 wherein the data processor is a computer capable of running at least a program for calibrating, rectifying and processing captured images.

15. The apparatus for 3-dimensional vision inspection according to claim 9 further including a third camera.

16. The apparatus for 3-dimensional vision inspection according to claim 15 wherein the third camera is placed in between the pair of first two cameras and is configured for inspecting another type of feature of the object, or another type of object.

17. The apparatus for 3-dimensional vision inspection according to claim 9 wherein a calibration reticle for having its image captured for calibration process is provided removably mounted.

18. The apparatus for 3-dimensional vision inspection according to claim 9 wherein the reflective surfaces are positioned at an inclination of 22.5° from parallel axis towards the object to be inspected so that said object is reflected into the cameras.

* * * * *